United States Patent [19]
Rhodes

[11] Patent Number: 5,872,151
[45] Date of Patent: Feb. 16, 1999

[54] IMMUNOPOTENTIATORY AGENTS AND PHYSIOLOGICALLY ACCEPTABLE SALTS THEREOF

[75] Inventor: John Richard Rhodes, Beckenham, England

[73] Assignee: Glaxo Wellcome Inc., N.C.

[21] Appl. No.: 813,915

[22] Filed: Mar. 7, 1997

Related U.S. Application Data

[63] Continuation of Ser. No. 462,115, Jun. 5, 1995, abandoned, which is a continuation of Ser. No. 224,152, Apr. 7, 1994, abandoned, which is a continuation-in-part of Ser. No. 112,849, Aug. 26, 1993, abandoned.

[30] Foreign Application Priority Data

| | | | |
|---|---|---|---|
| Oct. 1, 1992 | [GB] | United Kingdom | 9220715 |
| Dec. 23, 1992 | [GB] | United Kingdom | 9226874 |
| Sep. 17, 1993 | [GB] | United Kingdom | 93307373 |

[51] Int. Cl.$^6$ .................................................. A61K 31/19
[52] U.S. Cl. .............................................................. 514/568
[58] Field of Search ............................................. 514/568

[56] References Cited

U.S. PATENT DOCUMENTS 4,535,183   8/1985   Kneen .

FOREIGN PATENT DOCUMENTS

| | | |
|---|---|---|
| 0 054 924 A2 | 6/1982 | European Pat. Off. ............... 514/568 |
| 0 499 015 A1 | 8/1992 | European Pat. Off. . |
| 3508875 A1 | 11/1985 | Germany . |
| WO 92/03164 | 3/1992 | WIPO . |

OTHER PUBLICATIONS

Database Phind, Dialog Accession No. 321226, "Wellcome's Antisickling Agent Trial",Sep., 1992.
Rolan et al, Br. J. Clin. Phamacol, 35, No. 4, Apr. 1993.
Database Pharmaproject; PJB Publications Ltd., Richmond, Surrey, U.K.; Dialog Acc. Nr. 11933; May 4, 1993, tucaresol *abstract* & Pharmaprojects Updated May 4, 1993.
Database Phind: Pharmaceutical & Healthcare Industry News Database; Dialog accession No. 321226; Wellcome's antisickling agent trial; *abstract* & SCRIPT; vol. 1751, Sep. 2, 1992, p. 26. no date.
Int. J. Radia. Oncol. Biol. Phys.; vol. 16, No. 5, 1989; pp. 1179–1182; G.E. Adams et al.; Induction of severe tumor hypoxia by modifiers of the oxygen affinity of hemoglobin; the whole document.

European Search Report; International Application No. PCT/GB93/02039; Date of mailing Mar. 29, 1993; International filing date Sep. 30, 1993.
European Search Report; EP 93 30 7373; date of completion of search, Jan. 17, 1994.
I.J. Radiation Oncology Bio. Phys. vol. 16, pp. 1179–1182; may 1989; No. 5.; G.E. Adams, D. Sc., et al.; Induction of Severe Tumor Hypoxia by Modifiers of the Oxygen Affinity of Hemoglobin.
European Search Report PCT/GB91/01394; date of completion of search Nov. 20, 1991; date of mailing Dec. 4, 1991.
J. of Immunology vol. 143; pp. 1482–1489; No. 5; Sep.; John Rhodes Evidence for an Intercellular Covalent Reaction Essential Antigen–Specific T Cell Activation.
Radiotherapy & Oncology. vol. 16, 1989; pp. 235–243; Elseiver; Shirly Cole.
J. of Immunology, vol. 139; pp. 2845–2849; Nov. 1, 1987; R. Hess et al.; Immunosuppression by Succinulacetone.
Helv. Chim Acta 19: pp. 1095–1107 (1936); A. Girard and G. Sandulesco.
J. Lab Cln, Med. vol. 99; Nov. 4; pp. 526–532; Immunosupressive activity of succinylacetone.
J. Exp. Med. vol. 162; Sep. 1985; pp. 1060–1074; S. Manabe et al.; Hereditary Tyrosinemia.
Translation of European patent application Publication No. 0 217 041 A; Apr, 8, 1987; 6 pages.
American Cancer Society, vol. 45, No. 8 Aliza Adler et al.; pp. 2061–2073; Immunocompetence, Immunosuppression, and Human Breast Cancer.
Database Pharmaproject; PJB Publications Ltd.; Richmond, Surrey, U.K.; Dialog Acc. Nr. 11933; May 4, 1993, tucaresol *abstract* & Pharmaprojects Updated May 4, 1993.
Int. J. Radia. Oncol. Biol. Phys.; vol. 16, No. 5, 1989, pp. 1179–1182; G.E. Adams et al.; Induction of severe tumor hypoxia by modifiers of the oxygen affinity of hemoglobin; the whole document.

*Primary Examiner*—Jerome D. Goldberg
*Attorney, Agent, or Firm*—Graham & James LLP

[57] ABSTRACT

The present invention relates to the use of 4-(2-formyl-3-hydroxyphenoxymethyl) benzoic acid or physiologically acceptable salts thereof as an immunopotentiatory agent, compositions containing such a compound and their manufacture, combinations of such a compound with anti-tumour or anti-infective drugs and the use of such combinations in the prophylaxis or treatment of such diseases arising from tumours or infections.

7 Claims, 2 Drawing Sheets

IMMUNOPOTENTIATORY AGENTS AND PHYSIOLOGICALLY ACCEPTABLE SALTS THEREOF

This is a continuation of Ser. No. 08/462,115 filed on Jun. 5, 1995, now abandoned which is a continuation of application Ser. No. 08/224,152 filed on Apr. 7, 1994, now abandoned which is a continuation-in-part of U.S. Ser. No. 08/112,849 filed Aug. 26, 1993 now abandoned.

The present invention relates to the use of 4-(2-formyl-3-hydroxyphenoxymethyl) benzoic acid as an immunopotentiatory agent, compositions containing such a compound and their manufacture, combinations of such a compound with anti-tumour or anti-infective drugs and the use of such combinations in the prophylaxis or treatment of such diseases arising from tumours or infections.

European Patent No: 54924 discloses 4-(2-formyl-3-hydroxyphenoxymethyl)benzoic acid (the compound of formula (I):

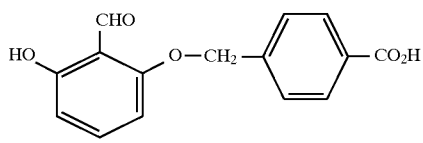

its synthesis and its properties as a "left-shifter" of the oxygen-dissociation curve. European Patent No. 54924 discloses that the compound of formula (I) increases the affinity of haemoglobin for oxygen causing transient hypoxia in normal and tumour tissue, and can be used in the radiosensitization of tumours. All references identified herein above or in the following are hereby incorporated by reference thereto. The generic name for the compound of formula (I) is tucaresol.

The principal protective function of the immune system relates to resistance to invasion by pathogens, including viruses, rickettsia, mycoplasma, bacteria, fungi and parasites of all types. Thus, improvement of immune response, particularly when depressed, improves resistance to infection or infestation by any of the above pathogens.

A second protective function of the immune system is to resist engraftment of foreign tissue, either natural or in fetal-maternal relationship; or unnatural as performed by the transplant physician.

A third protective function of the immune system is thought to be resistance to malignant cell development as in cancer. The use of immunopotentiators in cancer is logical to enhance tumour rejection and to inhibit tumour recurrences following other forms of therapy.

A fourth protective function involves maintaining non-reactivity to self by positive suppressor mechanisms. In auto-immune and related disorders, immune reactivity directed at self antigens or exaggerated, elevated responses are apparent which are self destructive.

Each of the protective functions of the immune system can be modified by nonspecific therapy with immunopotentiators alone or in combination with other agents employed to improve resistance or to kill the invading pathogen. In addition, specific resistance can be augmented by use of immunopotentiators in conjunction with some form of antigen as in a vaccine employing, for example, a virus, tumour cells, etc. This use can be to induce either specific immunity or tolerance. The latter is exemplified by use with an antigen in allergy or an auto-immune disease. Use of immunopotentiators may be either therapeutic or prophylactic; the latter is used particularly in the elderly, where infection, auto-immunity, and cancer are more common. The timing and route of administration are critical in determining whether a positive or negative response results. Any agent capable of augmenting an immune response may inhibit it depending on timing and dose; thus, under certain circumstances an immunopotentiator could be used as an immunosuppressive agent for use in allergy, auto-immunity and transplantation.

By immunopotentiator is meant an agent which is capable of restoring a depressed immune function, or enhancing normal immune function, or both. However because of certain elements of the immune system an immunopotentiator can also have immunosuppressive effects.

Immune responses are orchestrated by T-lymphocytes whose stereo-specific receptors are triggered by antigenic fragments bound to specialised molecules (MHC) on the surface of antigen presenting cells. In addition to the specific interaction between a T-cell receptor and antigen-MHC complex, T-cells require costimulatory signals which are provided by antigen-presenting cells. The interaction between antigen-presenting cells and T-cells involves accessory adhesion molecules some of which are linked to the T-cell receptor:antigen-MHC interaction and others which are separate from this interaction. Some of these adhesion molecules provide costimulatory signals. In addition, in vitro studies have established that transient covalent, chemical reactions between cell surface ligands are essential in the antigen-specific activation of T-cells Rhodes, J. (1989), J.Immunol. 143:1482; Gao, X. M. & Rhodes, J. (1990), J.Immunol. 144–2883; Rhodes, J. (1990), Immunol. 145:463). These take the form of a carbonyl-amino condensation (Schiff base formation) between groups on APC and T-cell surface.

It has now been found that the compound of formula (I) or physiologically acceptable salts thereof, surprisingly acts as an immunopotentiator.

In the salts of the compound of formula (I) the biological activity resides in ether (anion) moiety and the identity of the cation is of less importance although for use in medicine it is preferably pharmacologically acceptable to the recipient. Suitable salts include ammonium salts, alkali metal salts such as sodium and potassium salts, and salts formed with organic bases.

Therefore, the compound of the invention or physiologically acceptable salts thereof may be used for the treatment of diseases where there is a defect in the immune system and/or an ineffective host defence mechanism, or to enhance activity of the immune system above normal levels.

The present invention provides for the use of 4-(2-formyl-3-hydroxyphenoxymethyl) benzoic acid or physiologically acceptable salts thereof for the manufacture of a medicament for the potentiation of an immune response.

By potentiation of an immune response is meant restoration of a depressed immune function, enhancement of a normal immune function, or both. Immune function is defined as the development and expression of humoral (antibody-mediated) immunity, cellular (T-cell-mediated) immunity, or macrophage and granulocyte mediated resistance.

In this specification the term "immunodeficient patient" will be used to describe patients with a deficient or defective immune system. An immunodeficient patient can be characterised by means of a T-lymphocyte proliferation assay. Using this assay immunodeficient patients are characterised by a reduced ability of the T-cells to respond to stimulation by mitogens and recall antigens. An example of a mitogen commonly used in this assay is phytohaemagglutinin (PHA) and tetanus toxoid respectively.

In Adler et al., Cancer (1980) 45, 2062–2063 the immune function of breast cancer patients was evaluated by means of the T-lymphocyte proliferation assay using PHA. Quantitative estimation of the lymphocyte response to PHA was based on Stimulation Index (SI). In the aforementioned paper a SI value below 14 was defined to be below normal and thus these patients could be regarded as immunodeficient. Accordingly in this application we also consider that cancer patients who have a SI value below 14 are immunodeficient.

There is a variety of circumstances in which the immune system may be defective or deficient. Thus, for example immune system deficiency is common in immature or premature infants (neonates). It may also result from suppression by certain drugs, which may be deliberate e.g. as a side-effect of cancer chemotherapy. Disordered growth of one or more constituent parts of the immune system, e.g. as in certain forms of cancer, may also result in immunodeficiency. Immune deficiency may furthermore be caused by viral infections, including human immunodeficiency virus (HIV).

A further aspect of the present invention provides a method of treating immunodeficient patients, which comprises administering to a mammal (including human) an effective amount of the compound of formula (I), or a physiologically acceptable salt thereof. By an "effective amount" is meant the amount of the compound of formula (I) which will restore immune function to normal levels, or increase immune fuction above normal levels in order to eliminate infection.

The compound of formula (I) or physiologically acceptable salts may be administered for the treatment or prophylaxis of immunodeficient mammals alone or in combination with other therapeutic agents, for example, with other antiviral agents, or with other anticancer agents.

According to a further aspect of the present invention provides for the use of the compound of formula (I) or physiologically acceptable salts thereof for the treatment and/or prophylaxis of acute and chronic viral infections.

Examples of acute viral infections against which immunopotentiatory therapy with the compound of formula (I) or physiologically acceptable salts thereof may be used, preferably in conjunction with an antiviral agent, are:

Herpes viruses, influenza viruses, parainfluenza viruses, adenoviruses, coxsakie viruses, picorna viruses, rotaviruses, heptatitis A virus, mumps virus, rubella virus, measles virus, pox viruses, respiratory syncytial viruses, papilloma viruses, and enteroviruses, arenavirus, rhinoviruses, poliovirus, Newcastle disease virus, rabies virus, arboviruses.

Examples of chronic viral infections against which immunopotentiatory therapy with the compound of formula (I) or physiologically acceptable salts thereof may be used are:

Persistent herpes virus infections, Epstein Barr virus infection, persistent rubella infections, papovirus infections, hepatitis virus infections and human immunodeficiency virus infection.

The present invention is applicable to the treatment of viral hepatitis in all of its forms, five types now being recognised hepatitis A, B, C, D and E respectively.

Of the DNA viruses, those of the herpes group are the sources of the most common viral illnesses in man. The group includes herpes simplex virus (HSV), varicella zoster virus (VZV), cytomegalovirus (CMV); Epstein-Barr virus (EBV) and human herpes virus 6 (HHV6). HSV 1 and HSV 2 are some of the most common infectious agents of man. Most of these viruses are able to persist in the host's neural cells; once infected, individuals are at risk of recurrent clinical manifestations of infection which can be both physically and psychologically distressing.

HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the newborn, in immunocompromised patents including AIDS patients or penetration of the infection into the central nervous system, can prove fatal.

Varicella zoster (VZV) is a herpesvirus which causes chickenpox and shingles. Chickenpox is the primary disease produced in a host without immunity and in young children is usually a mild illness characterised by a vesicular rash and fever. Shingles or zoster is the recurrent form of the disease which occurs in adults who were previously infected with varicella-zoster virus. The clinical manifestions of shingles are characterised by neuralgia and a vescicular skin rash that is unilateral and dermatomal in distribution. Spread of inflammation may lead to paralysis or convulsions. Coma can occur if the meninges becomes affected. In immunodeficient patients VZV may disseminate causing serious or even fatal illness. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host and following a primary infection, virus may be shed for a number of years. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with HIV may give rise to retinitis, pneumoitis, gastrointestinal disorders and neurological diseases CMV infection in AIDS patients is a predominant cause of morbidity in 50–80% of the adult patient population, it is present in a latent form and can be re-activated in immunocompromised patients.

Epstein-Barr virus (EBV) causes infectious mononucleosis and hairy leukoplakis, and is also suggested as the causative agent of human cancer, such as nasopharyngeal cancer, immunoblastic lymphoma, Burkitt's lymphoma.

HBV is a viral pathogen of world-wide major importance. The virus is aetiologically associated with primary hepatocellular carcinoma and is thought to cause about 80% of the world's liver cancer. In the United States more than ten thousand people are hospitalised for HBV illness each year, and average of 250 die with fulminant disease. The United States currently contains an estimated pool of 500,000 to 1-million infectious carriers. Chronic active hepatitis generally develops in over 25% of carriers, and often progresses to cirrhosis. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

Of the RNA viruses, one group has assumed a particular importance this is the retroviruses. Retroviruses form a sub-group of RNA viruses which, in order to replicate, must first 'reverse transcribe' the RNA of their genome into DNA ('transcription' conventionally describes the synthesis of RNA from DNA). Once in the form of DNA, the viral genome may be incorporated into the host cell genome, allowing it to take advantage or the host cell's transcription/translation machinery for the purposes of replication. Once incorporated, the viral DNA is virtually indistinguishable from the host's DNA and, in this state, the virus may persist for the life of the cell.

In the case of immunosuppression resulting from HIV infection, prophylaxis may be required by those diagnosed as seropositive for HIV i.e. having antibodies to HIV, and those with PGL (progressive generalised lymphadenopathy) or ARC (AIDS-related complex) as well as patients suffering from AIDS or patients suffering from AIDS-like immune deficiencies where the HIV infection is not detectable and who also require immunorestoration by means that are not specific to any particular virus.

The compounds according to the invention may be employed alone or in combination with other therapeutic agents for the treatment of the above infections or conditions. Combination therapies according to the present invention comprise, the administration of at least one compound of the formula (I) or a physiologically functional derivative thereof and at least one other pharmaceutically active ingredient. The active ingredient(s) and pharmacologically active agents may be administered together or separately and, when administered separately this may occur simultaneously or sequentially in any order. The amounts of the active ingredient(s) and pharmacologically active agents(s) and the relative timings of administration will be selected in order to achieve the desired combined therapeutic effect. Preferably the combination therapy involves the administration of one compound of the formula (I) or a physiologically functional derivative thereof and one of the agents mentioned herein below.

Examples of such further therapeutic agents include agents that are effective for the treatment of HIV infections or associated conditions such as 3'-azido-3'-deoxythymidine (zidovudine), other 2',3'-dideoxynucleosides such as 2',3'-didoxycytidine, 2',3'-dideoxyadenosine and 2',3'-didoxyinosine, carbovir; acyclic nucleosides (for example, acyclovir), 2',3'-didehydrothymidine, protease inhibitors such as N-tert-butyl-dechydro-2-[-2(R)-hydroxy-4-phenyl-3 (S)-[[N-2-quinolyl-carbonyl)-L-asparginyl]butyl]-(4aS,8aS) -isoquinoline-3(S)-carboxamide (Ro 31-8959), oxathiolan nucleoside analogues such as cis-1-(2-hydroxymethyl)-1,3-oxathiolan-5-yl)-cytosine or cis-1-(2-(hydroxymethyl)-1,3-oxathiolan-5-yl)-5-fluoro-cytosine, 3'-deoxy-3'-fluorothymidine, 2',3'-dideox-5-ethynyl-3'-fluorouridine, 5-chloro-2',3'-dideoxy-3' fluorouridine, Ribavirin, 9-[4-hydroxy-2-(hydroxymethyl)but-1-yl]guanine (H2G), TAT inhibitors such as 7-chloro-5-(2-pyrryl)-3H-1,4-benzodiazepin-2(H)-one (Ro5-3335), or 7-chloro-1,3-dihydro-5-(1H-pyrrol-7-yl)-3H-1,4-benzodiazepin-2-amine (Ro24-7429) interferons such as α-interferon, renal excretion inhibitors such as probenecid, nucleoside transport inhibitors such as dipyridamole; pentoxifyline, NAcetylCysteine, Procysteine, α-trichosanthin, phosphonoformic acid, as well as immunodulators such as interleukin II, granulocyte macrophage colony stimulating factors, erythropoetin, soluble $CD_4$ and genetically engineered derivatives thereof. Examples of such further therapeutic agents which are effective for the treatment of HBV infections include carbovir, oxathiolan nucleoside analoges such as cis-1-(2-hydroxymethyl)-1,3-oxathiolan-5-yl)-cytosine or cis-1-(2-(hydroxymethyl)-1,3-oxathiolan-5-yl-5-fluorocytosine, 2',3'-didoxy-5-ethynyl-3'-fluorouridine, 5-chloro-2',3'-didoxy-3'-fluorouridine, 1-(β-D-arabinofuranoysl)-5-propynyluracil, acyclovir and interferons, such as α interferon.

It has been reported (Hughes, W. T. (1987) Treatment and Prophylaxis of *Pneumocystis carinii* pneumonia, Parasitology Today 3(11) 332–335) that at least 60% of patients with acquired immunodeficiency syndrome (AIDS) suffer from *Pneumocystis carinii* pneumonia.

Without treatment, *Pneumocystis carinii* pneumonia is almost always fatal in immunocompromised hosts. The most widely used treatments for this condition are trimethoprim-sulphamethoxazole (cotrimoxaole) and pentamidine. However, both of these treatments have been reported to be only around 50–70%, effective in AIDS patients and to produce a much higher than usual incidence of adverse reactions (about 50%) (Wofsy, C. B. Antimicrobial Agents Annual, 1986, Vol 1, p377–400). There is thus a need for new agents, especially for the prophylaxis of *P.carinii* pneumonia.

In another aspect the present invention provides the use of the compound of formula (I) and physiologically acceptable salts thereof for the manufacture of a medicament for the treatment and/or prophylaxis of *Pneumocystis carinii* infections in mammals (including humans).

In a yet further aspect the present invention provides for the use of the compound of formula (I) and physiologically acceptable salts thereof to treat conditions resulting from relative or absolute T-cell deficiencies such as DiGeorge Syndrome, fungal infections, mycoplasma infections, tuberculosis, leprosy, and systemic lupus erythemotosus.

In another aspect of the present invention provides for the use of the compound of formula (I) and physiologically acceptable salts thereof for the manufacture of a medicament for the treatment and/or prophylaxis of cancer in mammals including humans).

In a further aspect of the present invention provides for the use of the compound of formula (I) and physiologically acceptable salts thereof for the manufacture of a medicament for the treatment and/or prophylaxis of cancer other than radiotherapy.

Figure 1:
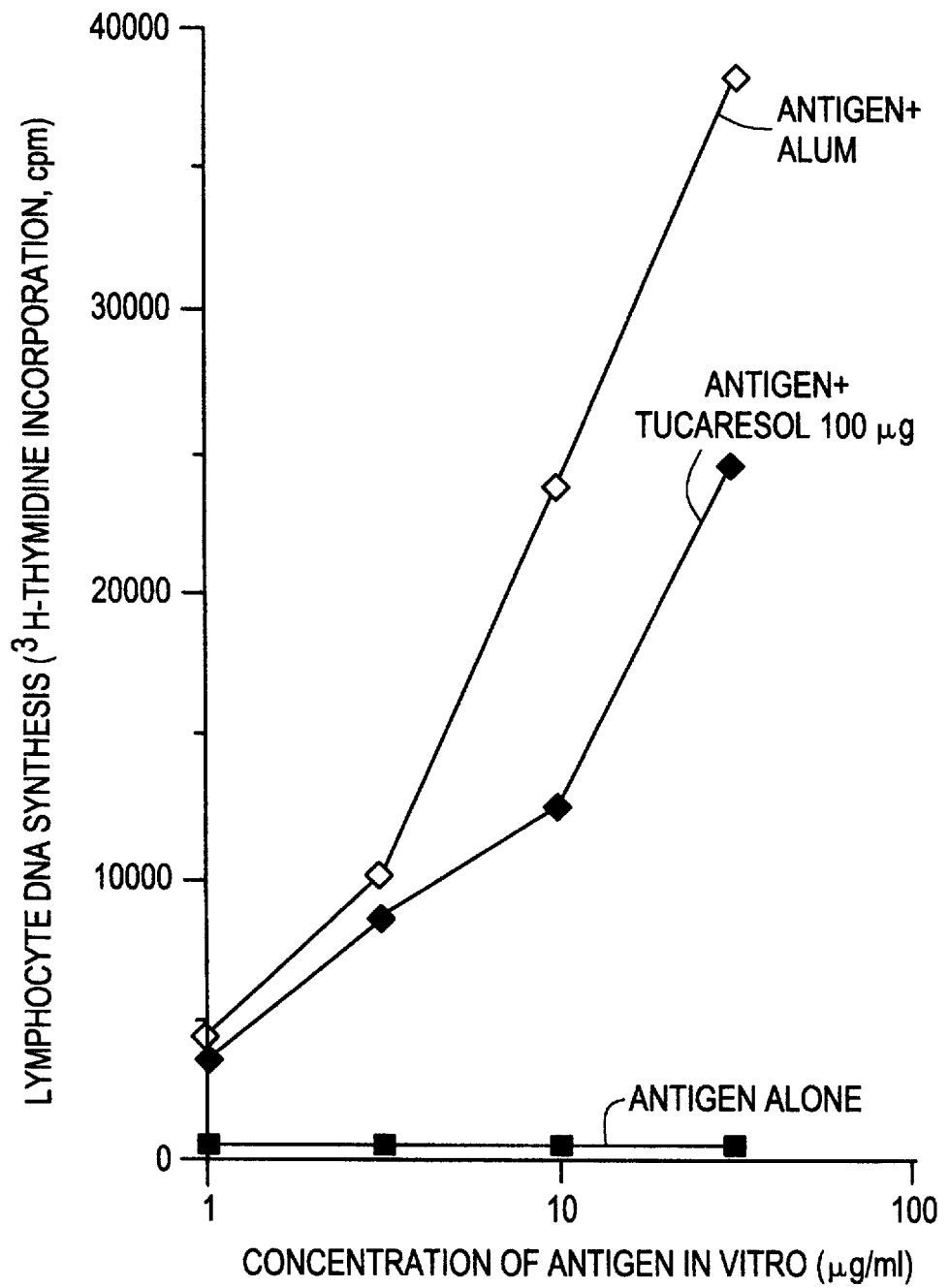
FIG. 1 is a comparative graph showing concentration of antigen in vitro relative to lymphocyte DNA synthesis for antigen with conventional adjuvant alum and antigen+ tucaresol.

The compound of formula (I) or physiologically acceptable salts thereof can also be used for the treatment and prophylaxis of cancer, at a daily dosage substantially lower and for a longer duration than the dosage used previously disclosed in EP 54924. The duration of dosing for the treatment and prophylaxis of cancer using a compound of the invention is longer than would be required for radiosensitisation.

Examples of forms of cancers particularly suitable for treatment with the compound of formula (I) are: melanoma, cervical cancer, breast cancer, colon cancer, cancer of the head and neck, gastric cancer, renal cancer, laryngeal cancer, rectal cancer, and non-Hodgkins lymphoma. Cancers that express tumour specific antigens or antigens rarely expressed or expressed at very low density on normal cells, are likely therapeutic targets. Cancers which contain tumour specific cytotoxic T-cells which are anergic or otherwise ineffective are likely targets for therapy. Surgically resected tumours where there is a high risk of recurrence are also suitable for therapy with the compound of formula (I). Also early stage cancer patients with minimal disease or localised disease are suitable for therapy.

The compound of formula (I) is thought to act by providing a co-stimulatory signal to cloned (partially) activated T-cells in vitro, thus maximally activating T-cells.

A further aspect of the present invention provides for the use, as a vaccine adjuvant, of the compound of formula (I) or physiologically acceptable salts. A vaccine may therefore be prepared by formulating the antigenic component with the compound or formula (I).

The compound or formula (I) may be administered to the human recipient by a route selected from oral, parenteral (including subcutaneous, intradermal, intramuscular and intravenous), rectal and inhalation. The size of an effective dose of a compound will depend upon a number of factors including the identity of the recipient, the type of immuno-potentiation involved, the severity of the condition to be treated and the route of administration, and will ultimately be at the discretion of the attendant physician.

For each of the aforementioned conditions, such an effective dose will generally be in the range 0.5 to 50 mg/kg bodyweight of human recipient per day, preferably in the range 1 to 20 mg/kg bodyweight per day and most preferably in the range 1 to 10 mg/kg bodyweight per day; an optimum dose is 3 mg/kg bodyweight per day. The above doses are for a human usage.

The desired dose may be presented as between two and four sub-doses administered at appropriate intervals throughout the day. Thus where three sub-doses are employed each will generally lie in the range 0.03 mg to 33 mg, preferably 16 mg to 166 mg and most preferably 0.3 to 6.6 mg (acid)/kg bodyweight with an optimum of 1.0 mg (acid)/kg bodyweight. A daily dose for a human weighing of the order of 50 kg will thus generally lie in the range 5 mg to 5 g (acid), preferably in the range 25 mg to 2.5 g (acid) and most preferably in the range 50 mg to 1 g (acid). Optimally a human daily dose is 150 mg (acid). The desired dose is preferably presented as a daily dose, over a period of at least 5 days, most preferably over a period of at least 28 days.

While it is possible for the compound of formula (I) to be administered as the raw chemical it is preferable to present them as a pharmaceutical formulation preparation. The formulations of the present invention comprise a compound of formula (I), as above defined, together with one or more acceptable carriers therefor and optionally other therapeutic ingredients. The carrier(s) must be 'acceptable' in the sense of being compatible with the other ingredients of the formulation and not deleterious to the recipient thereof.

The formulations include those suitable for oral, parenteral (including subcutaneous, intradermal, intramuscular and intravenous) and rectal administration although the most suitable route may depend upon for example the condition of the recipient. The formulations may conveniently be presented in unit dosage form and may be prepared by any of the methods well known in the art of pharmacy. All methods include the step of bringing into association the compound of formula (I) (the active ingredient) with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression, or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Formulations for rectal administration may be presented as a suppository with the usual carriers such as cocoa butter.

European Patent No. 54924 contains no invitation to administer the compound of formula (I) by the nasal or pulmonary route nor any suggestion that the said compound, if administered in such a manner, would be effective in the treatment of the conditions therein taught; the said disclosure likewise contains no description of any formulation suitable for administration by the nasal or pulmonary route.

Formulations suitable for pulmonary administration via the buccal cavity are presented such that particles containing the active ingredient and desirably having a diameter in the range 0.5 to 7 microns are delivered into the bronchial tree of the recipient.

As one possibility such formulations are in the form of finely comminuted powders which may conveniently be presented either in a pierceable capsule, suitably of for example gelatin, for use in an inhalation device, or alternatively as a self-propelling formulation comprising active ingredient, a suitable liquid propellant and optionally other ingredients such as surfactant and/or a solid diluent. Self-propelling formulations may also be employed wherein the active ingredient is dispensed in the form of droplets of a solution or suspension.

Such self-propelling formulations are analogous to those known in the art and may be prepared by established procedures. Suitably they are presented in a container provided with either a mannually-operable or automatically functioning valve having the desired spray characteristics; advantageously the valve is of a metered type delivering a fixed volume, for example 50 to 100 microliters, upon each operation thereof.

As a further possibility the active ingredient may be in the form of a solution for use in an atomiser or nebuliser whereby an accelerated airstream or ultrasonic agitation is employed to produce a fine droplet mist for inhalation.

Formulations suitable for nasal administration include presentations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of the active ingredient in aqueous or oily solution.

Preferred unit dosage formulations are those containing an effective dose, as hereinabove recited, or an appropriate fraction thereof, of the active ingredient.

The following Examples are provided in illustration of the present invention and should not be construed as in any way constituting a limitation thereof. All temperatures are in degrees Celsius.

| Solution for nebulisation | |
|---|---|
| Compound of formula (I) | 1.0 mg |
| Water for injections to | 10.0 mL |

Dissolve the compound of formula (I) as for injections. Sterilize the solution by passage through a membrane filter, 0.21 m pore size, collecting the filtrate in a sterile receiver. Fill into sterile glass ampoules, 10 mL/ampoule, under aseptic conditions and seal each ampoule by fusion of the glass.

| Self-propelling formulation | |
|---|---|
| Compound of formula (I), micronised | 1.0 mg |
| Propellant to | 5.0 mL |

Suspend the micronised compound of formula (I) in the propellant. Fill this suspension under pressure into preformed, valved aerosol canisters, 5 mL/canister, through the valve orifice.

The propellant is a commercially available mixture of trichloromono-fluoromethane, dichlorodifluoromethane and dichlorotetrafluoroethane.

| Powder for inhalation | |
|---|---|
| Compound of formula (I), micronised | 1.0 mg |
| Lactose | 29.0 mg |

Triturate and blend the micronised compound of formula (I) with the lactose. Fill the resulting powder blend into hard gelatin capsule shells, 30 mg per capsule. Alternatively, the micronised compound of formula (I) could be compressed into a plug and a device which delivers small amounts of the compound of formula (I) into the airstream can be used.

| Nasal drops | |
|---|---|
| Compound of formula (I) | 100 mg |
| Methyl p-hydroxybenzoate | 10 mg |
| Water for injections to | 10 mL |

Dissolve the compound of formula (I) and the methyl p-hydroxybenzoate in the water for injections. Fill this solution into suitable dropper bottles. 10 mL/bottle, and close by securing the dropper nozzle and bottle cap.

| Tablet | |
|---|---|
| Compound of formula (I) | 100 mg |
| Lactose | 100 mg |
| Starch | 50 mg |
| Polyvinylpyrrolidone | 5 mg |
| Magnesium Stearate | 5 mg |
| | 260 mg |

The Compound, Lactose and Starch are mixed together and then granulated with a solution of Polyvinyl-pyrrolidone in water. After drying the granules, the Magnesium Stearate is mixed in and tablets compressed at an average weight of 260 mg.

| Capsule | |
|---|---|
| Compound of formula (I) | 100 mg |
| Dibasic Calcium Phosphate Dihydrate | 100 mg |
| Sodium Starch Glycolate | 16 mg |
| Methylcellulose 400 cps | 5 mg |
| Stearic Acid | 4 mg |
| Talc | 5 mg |
| | 230 mg |

The Compound, Dibasic Calcium Phosphate, Dihydrate and Sodium Starch Glycolate are mixed together and then granulated with a solution of the Methylcellulose in water. After drying, the granules are mixed with the Stearic Acid and Talc and the mixture filled into gelatin capsules at an average fill weight of 230 mg.

| Suppository | |
|---|---|
| Compound of formula (I) | 100 mg |
| Suppository Base (Mixed Glycerides of saturated fatty acids) | 1700 mg |
| | 1800 mg |

Grind the Compound to a particle size below 150$\mu$. Add the suppository base at 38°–40° C. Mix to give a uniform dispersion. Pour into suppository moulds and allow to cool.

| Injection - Single dose intravenous | |
|---|---|
| Compound of formula (I) | 100 mg |
| Sodium Hydroxide Solution (30%) | q.s. |
| Water for Injections to | 5 mL |

Suspend the Compound in some of the Water for Injections. Adjust the pH to 10 to 10.5 by addition of Sodium Hydroxide Solution. Add sufficient Water for Injections to produce the required final volume. Re-check the pH. Sterilise by passage through a sterile membrane filter of 0.22μ pore size. Fill under aseptic conditions into sterile vials and freeze dry.

| Injection - Multidose, intramuscular | |
|---|---|
| Compound of formula (I), sterile | 1000 mg |
| Polysorbate 20 | 3 mg |
| Polyvinylpyrrolidone | 1000 mg |
| Chlorocresol | 60 mg |
| Sodium Chloride | q.s. to isotonicity |
| Water for Injections to | 30 mL |

Dissolve the Polysorbate 20, Polyvinylpyrrolidone, Sodium Chloride and Chlorocresol in Water for Injections. Sterile filter, 0.22μ. Grind the sterile Compound to a particle size below 20μ and add to the filtered solution. Mix until a uniform dispersion is achieved. Fill into sterile glass vials.

| Prolonged Release Tablet | |
|---|---|
| Compound of formula (I) | 200 mg |
| Casein | 195 mg |
| Hydrogenated Castor Oil | 400 mg |
| Magnesium Stearate | 5 mg |
| | 800 mg |

Melt the Hydrogenated Castor Oil and add the Compound, ground to a particle size of less than 150μ. Add the Casein. Mix until uniform. Allow to cool and mill to a granule. Mix in the Magnesium Stearate and compress to an average weight of 1,200 mg.

In the foregoing the "Compound" refers to a compound of formula (I) as hereinbefore defined.

Preferred unit dosage formulations are those containing a daily dose or unit daily sub-dose, as hereinabove recited, or an appropriate fraction thereof, of a compound of formula (I) or physiologically acceptable salts thereof.

It should be understood that in addition to the ingredients particularly mentioned above the formulations of this invention may include other agents conventional in the an having regard to the type of formulation in question, for example those suitable for oral administration may include flavouring agents.

The compound of formula (I) or physiologically acceptable salts thereof may also be presented as depot formulations of the kind known in the art from which the active ingredient is released, over a prolonged period, once the formulation is in place within the body of the recipient.

The results of tests with the compound of formula (I) are described in the following Experimental examples in order to illustrate the effect of the present invention in more detail.

EXAMPLE 1

Mice were injected subcutaneously in the dorsal mid-line either with antigen alone, with antigen plus a conventional adjuvant, or with antigen plus test compound. Subsequent additional injections of test compound were also given where specified for up to four days at the same injection site. After seven days regional (inguinal) lymph nodes were removed and the lymph node cells restimulated with antigen alone. Antigen specific proliferation of lymphocytes was measured after a further four days by a standard procedure employing $^3$H-thymidine uptake into DNA and liquid scintillation spectrometry. Tests for humoral immunity were performed by administering antigen and test compounds in the same way. After 1–2 weeks blood was sampled by venepuncture and serum antibody was assayed by an enzyme-linked immunosorbent (ELISA) assay.

RESULTS

The data in FIG. 1 show the effects of the compound of formula (I) on T-lymphocyte priming to antigen (keyhole limper haemocyanin). BIOS mice received 50 μg of antigen either alone (■), with the conventional adjuvant alum (◇), or with 100 μg of compound of formula (I) (♦). Compound of formula (I) is also known as tucaresol.

EXAMPLE 2

Antitumour Activity of the Compound of Formula (I)

The activity of the compound of formula (I) was evaluated against the outgrowth of subcutaneously implanted mouse colon adenocarcinoma 33 (MCA38) in female C57BL/6 mice, using the following protocol:

Day 0 Forty, 7-week-old female C57BL/6 mice each implanted subcutaneously with one 2 mm cube of tumour.

Day 12 19 mice each with palpable tumours (4 to 6 mm diameter) selected from above group, randomized and assigned to either the test group (10 animals) or the control group (9 animals).

Day 13 Test group each dosed with the compound of formula (I) (1 mg per mouse dissolved in 0.2 ml PBS, intraperitoneally) once every alternate day (total of 7 doses), Day 27 All mice killed, tumours excised and weighed. Mean tumour weight in test group compared with that in controls.

The compound of formula (I) was dissolved in PBS by dropwise addition of 1M KOH to pH 10.0 followed by dropwise addition of conc. HCl to return pH to neutral. Solutions were injected within 1 hour of preparation.

Dosing schedule where drug was given on alternate days was chosen in order to extend the dosing period over 14 rather than 7 days. By so doing tumours were exposed to the drug from day 13 right up until day 25 (i.e. 2 days before the experiment was terminated). Results are shown in Table 1.

The pattern of tumour growth (diffuse granular) rendered calliper measurements of volume, meaningless and such data are therefore not included.

EXAMPLE 3

Systemic (intraperitoneal) administration of tucaresol to produce immunopotentiation.

Figure 2:
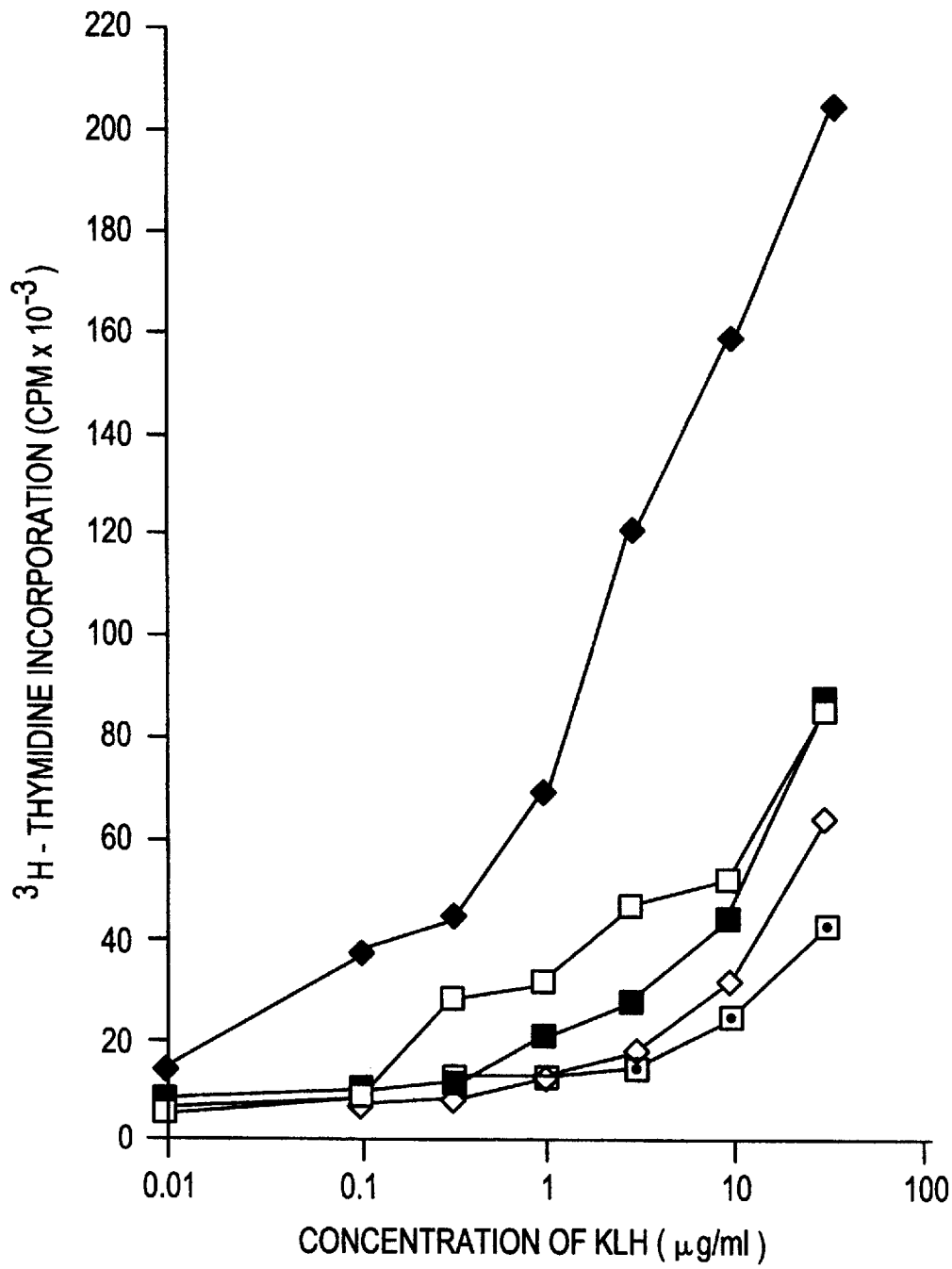
FIG. 2 is a comparative graph showing concentration of KLH relative to 3H-thymidine incorporation for various administered concentrations of tucaresol including a control.

Eight week old female Balb/c mice received five daily injections of tucaresol each containing either 100 μg, (□) 200 μg (♦) or 1 mg (◇) of the drug intraperitoneally starting on day 0. A control group received no drug (■). All mice were immunized subcutaneously on day 0 with 5 μg of KLH. An additional control group received no drug and no KLH (▣). On day 1, concurrent with the second i.p. injection of drug mice were immunised subcutaneously in the dorsal mid-line at the base of the tail with 10 μg of Keyhole limpet haemocyanin (KLH). On day 7 regional (inguinal) lymph nodes were removed and the lymph node cells restimulated with KLH in vitro. Proliferation was measured 4 days later by the incorporation of $^3$H-thymidine into DNA. This provided a sensitive specific measure of the T-cell priming that has occurred in vivo. The results are shown in FIG. 2. The results show that the dose of tucaresol required to produce immunopotentiation in this way is at least fivefold lower than the dose required for left-shift effects on haemoglobin and that the latter high doses are in fact much less effective in immunopotentiation than low doses.

Effect of tucaresol (4-(2-formyl-3-hydroxyphenoxymethyl)benzoic acid) treatment on SIV infection in cynomolgus macaques.

Four cynomolgus macaques (*Macaca fascicularis*) of average weight of 2.5 kg with established SIV infection were used in this study. Two animals were dosed with tucaresol at 30 mg/kg every other day for 9 days by intraperitoneal injection (5 injections total). The two untreated animals received control injections of saline. The treatment resulted in splenic enlargement in both treated animals, one of which also developed a general malaise which resolved over the next few days. Viral load was measured on day eleven (two days after cessation of treatment). In the untreated controls, $10^{3.5}$ viral units were detected per $10^6$ blood leukocytes in both animals. In the treated animal who had no malaise $10^{2.5}$ viral units per $10^6$ leukocytes were detected (i.e. a tenfold reduction in comparison with the two controls). In the treated animal who had signs of malaise, no virus was detectable by the conventional assay.

TABLE 1

| | TUMOR WEIGHT g. | |
|---|---|---|
| | Compound of formula (I) | Untreated Controls |
| | 1.44 | 1.66 |
| | 0.77 | 1.45 |
| | 0.72 | 1.43 |
| | 0.48 | 1.14 |
| | 0.43 | 0.56 |
| | 0.39 | 0.32 |
| | 0.28 | 0.26 |
| | 0.13 | 0.17 |
| | 0.06 | Died |
| | 0.03 | — |
| MEAN WEIGHT g (SD) | 0.473(0.423) | 0.868(0.50) |

TABLE 1-continued

| | TUMOR WEIGHT g. | |
|---|---|---|
| | Compound of formula (I) | Untreated Controls |
| MEAN % REDUCTION TUMOUR OUTGROWTH TREATED v CONTROLS | | 45.4 |
| MEDIAN WEIGHT | 0.41 | 0.85 |
| MEDIAN % REDUCTION TUMOUR OUTGROWTH TREATED v CONTROLS | | 51.77 |

The compound of formula (I) inhibited the outgrowth of subcutaneously implanted MCA38 in syngeneic C57BL/6 mice.

I claim:

1. A method for treating virus infections in an immunodeficient mammal in need thereof, which comprises administering to said mammal an effective immunopotentiatory amount of 4-(2-formyl-3-hydroxyphenoxymethyl)benzoic acid or a physiologically acceptable salt thereof, over a period of at least 5 days for the potentiation of an immune response.

2. The method according to claim 1, wherein the immunodeficient mammal is human having a Stimulation Index below 14.

3. The method according to claim 1, wherein the effective amount is from 50 to 200 mg per day.

4. The method according to claim 1, wherein the effective amount can be administered on alternate days.

5. The method according to claim 2, wherein the effective amount is from 50 to 200 mg per day.

6. The method according to claim 3, wherein the effective amount can be administered on alternate days.

7. A method of reducing viral load of immunodeficiency viruses in the blood of a mammal having said viruses comprising administering to said mammal an effective viral load reducing amount of 4-(2-formyl-3-hydroxyphenoxymethyl)benzoic acid or a physiologically acceptable salt thereof.

* * * * *